Figure 1:
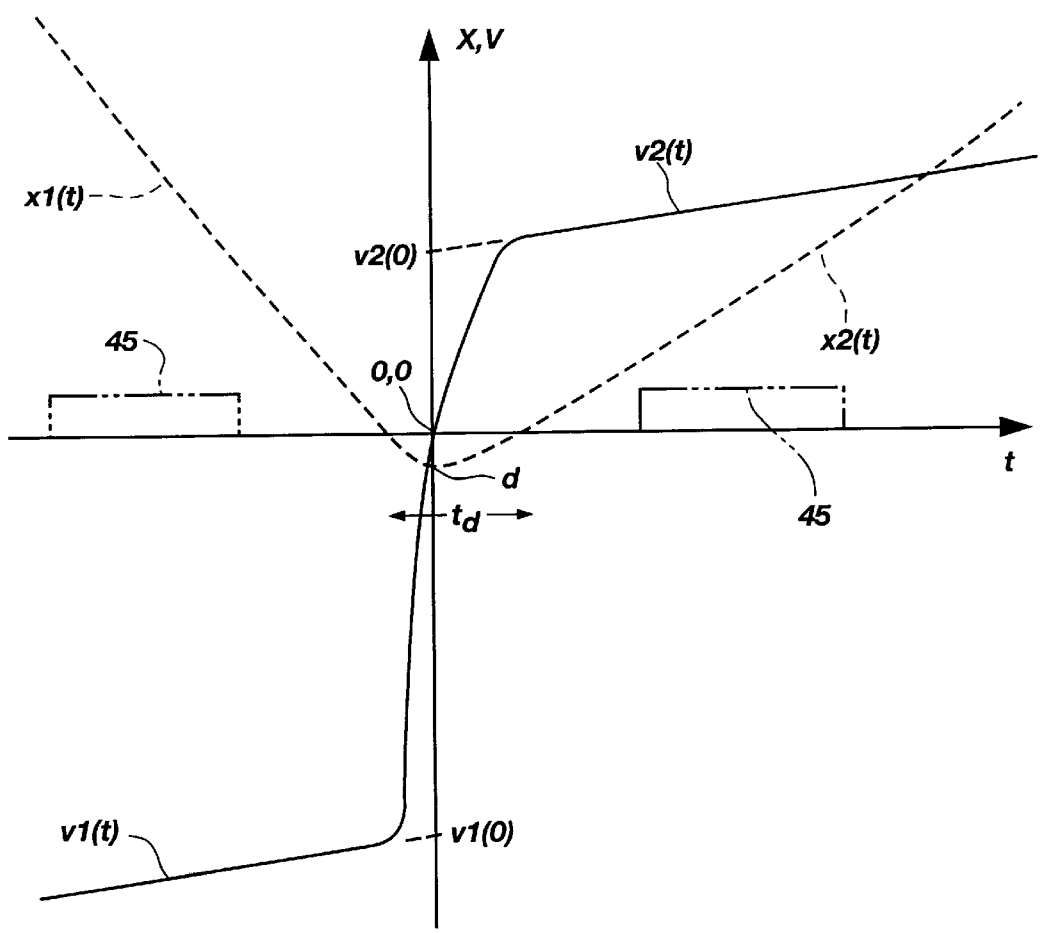

United States Patent [19]
Pollok et al.

[11] Patent Number: 5,959,198
[45] Date of Patent: Sep. 28, 1999

[54] METHOD AND DEVICE FOR TESTING THE HARDNESS OF WORKPIECES AND DEVICE FOR CARRYING OUT THIS PROCESS

[76] Inventors: Heinz-Horst Pollok, Aachener Str. 38, D-50389 Wesseling; Andreas Wiese, Waldstrasse 27, D-53177 Bonn, both of Germany

[21] Appl. No.: 08/945,407
[22] PCT Filed: Apr. 16, 1996
[86] PCT No.: PCT/DE96/00562
§ 371 Date: Jan. 12, 1998
§ 102(e) Date: Jan. 12, 1998
[87] PCT Pub. No.: WO96/34267
PCT Pub. Date: Oct. 31, 1996

[30] Foreign Application Priority Data

Apr. 27, 1995 [DE] Germany ............................ 195 14 857

[51] Int. Cl.⁶ ...................................................... G01N 3/30
[52] U.S. Cl. ............................. 73/79; 73/12.06; 73/12.09
[58] Field of Search ............................... 73/12.01, 12.04, 73/12.06, 12.09, 12.11, 12.13, 78, 79

[56] References Cited

U.S. PATENT DOCUMENTS

| | | | |
|---|---|---|---|
| 3,879,982 | 4/1975 | Schmidt | 73/79 |
| 4,034,603 | 7/1977 | Leeb et al. | 73/79 |
| 4,411,153 | 10/1983 | Lewis | 73/79 |
| 5,176,026 | 1/1993 | Leeb et al. | 73/79 |
| 5,176,139 | 1/1993 | Fedorov et al. | 73/79 |
| 5,457,984 | 10/1995 | Ambur et al. | 73/12.09 |

*Primary Examiner*—Max H. Noori
*Attorney, Agent, or Firm*—K. S. Cornaby

[57] ABSTRACT

The invention concerns a method of testing the hardness of workpieces (22), wherein an impact body (20) is moved onto the workpiece (22) to be tested such that it impinges thereon (along a forward path) and rebounds thereof (along a return path). On both the return and the forward paths, a movement value of the impact body (20) is detected by a contactlessly operating device and a measure of the hardness of the workpiece (22) is obtained from the difference between the forward and return path movement values. The movement value is detected at at least two points on the forward path and at at least two points on the return path. Corresponding to each movement value detection point on the forward path is a point on the return path at a substantially similar distance from the point of impact.

9 Claims, 2 Drawing Sheets

METHOD AND DEVICE FOR TESTING THE HARDNESS OF WORKPIECES AND DEVICE FOR CARRYING OUT THIS PROCESS

The invention relates to a procedure for a hardness test of workpieces, with which an impact object is moved onto the workpiece to be tested in such a way, that it strikes onto the same (on the forward path) and (on the backward path) rebounds again off it, whereby on the forward path and on the backward path a quantity of motion of the impact object is recorded each by means of a device working without contact and a measurement is received for the hardness of the workpiece by the difference of the quantity of motion of the forward path and that of the backward path and a device for the operation of this procedure.

From the procedure of the above mentioned kind known from the DE 24 52 880 C2 as well as from the devices working according to these procedures, the impact object is connected to a permanent magnet, which can be moved via an induction coil, which itself is connected to a tubular case, within which the impact object is movable. In the known procedure the quantities of motion are recorded directly before the impact and directly after the rebound. In the practical application, however, it is necessary to keep a certain distance from the location of the impact, a measurement of the quantities of motion directly at the time of impact cannot be performed. For the evaluation it is necessary, however to extrapolate to the time of impact or the location of impact. The closer the measurement is performed at the location of impact, the easier it is.

The further the quantities of motion are recorded from the location of impact, however, the bigger the influence of other parameters, especially that of the forces of gravity. It is evident that with the known equipment of the above mentioned kind, the distance between the location of impact and the location, at which the quantity of motion is measured, is so relevant already that the forces of gravity have an importance which should not be neglected. The kinds of equipment already on the market mentioned above are equipped with correction charts for their orientation. These charts exist either in printed form or they are stored in the equipment and have to be read or selected at the time of evaluation. So it is especially important, whether the impact object is moved from below, against the forces of gravity, towards the workpiece and falls back under the influence of the forces of gravity or vice versa, whether the forces of gravity accelerate the impact object on the forward path and reduce the speed by braking on the backward path, meaning that the equipment is mounted upon the workpiece to be tested from above.

The correction procedure according to the state of the art make the use of the known equipment circumstantial, they make the application much harder for the user. Furthermore the correction procedures are also a reason for incorrect measurements, because the corrections are not taken into account correctly, because, for example, the actual angle between the equipment and the vertical line is met in the wrong way.

This is where the invention sets in. It is the task of the invention to further develop the procedure of the above mentioned kind and the equipment for the hardness test working according to this procedure in such a way, that the forces of gravity are already taken into account at the time of measurement, and that correction charts can be avoided in such a way.

This task is solved according to the procedure of the above mentioned kind in such a way that the quantity of motion is recorded at two locations of the forward path at least and at two locations of the backward path at least and that each location of the forward path, where the quantity of motion is recorded, corresponds to a location of the backward path each with the same distance of the impact location, if possible.

This task is solved by an equipment for a hardness test according to patent claim 6 with regard to the device.

Unlike to the procedure and the respective equipment according to the state of the art, the invention does not aim to record the quantity of motions in the possible direct vicinity of the location of the impact, if possible. It much rather records the quantity of motions at at least two different locations on the forward path as well as on the backward path.

These may have a certain distance from the location of the impact though and it is preferred to perform the measurement at those locations, where there is an especially good signal, for example a maximum of an induction tension in case that the quantity of motion is recorded via an electromagnetic device.

It has proven to be especially advantageous, if the at least two locations, on which the quantity of motion is recorded along the backward path, each have exactly the same distance from the location of the impact as the at least two locations of the backward path. As has become obvious that the velocity of the impact object is not only a function of the time but also a function of the location. If one measures the quantity of motion, which is connected with the velocity in one way or the other, at the same location on the forward path and on the backward path, then the influence of the location can be eliminated by the quotient formation.

Basically it is possible, however, that a measurement of the quantity of motions occurs on the backward path at other locations than on the forward path. When checking the workpieces of a lesser hardness, problems might occur.

The more measurements of the quantity of motion are performed on the forward path and on the backward path, the more precisely the path of the motions can be calculated during the forward path and during the backward path, the more precisely the velocity of the impact object can be extrapolated on the forward path at the location of impact and on the backward path at the location of impact. The quotient of these two extrapolated velocities is proportional to the hardness rate to be determined. A measurement of the quantity of motion at three locations each or at more locations of the forward path and the backward path is therefore advantageous.

In a preferred embodiment the quantity of motion is recorded electromagnetically, whereby the impact object has a permanent magnet, and a tubular case is provided, in which the impact object is movable and which carries an induction coil. When the induction coil falls through, the permanent magnet induces a tension, from which the quantity of motion can be deducted. The allocation, which induced value of the tension exists at which location, is gained by further measurements, for example a light screw and/or via a zero crossing of the induced tension.

Further advantages and characteristics of the invention derive from the other claims as well as the following description of a non-restrictive embodiment of the invention, which is illustrated further with regard to the drawing. This drawing shows in:

FIG. 1: A diagram of the velocity v and the path x of the impact object during the period of time t during a measurement process, FIG. 2: a diagram according to FIG. 1 for the process of time of the induction tension u(t) at a measurement process, FIG. 3: a principal illustration of the device used for the operation of the procedure, FIG. 4: an illustration according to FIG. 3 for an altered device and FIG. 5: an illustration according to FIG. 3 for a device altered again.

FIG. 1 illustrates the process of time of the velocity and the path of an impact object 20 at a typical measurement process. The designations used can also be seen in this illustration. It can be seen from the curve of the path, which is illustrated in a dotted line, that there is a penetration for a certain period of time, the duration of the penetration has the designation td, the penetration occurs with a depth of penetration d. The actual time of impact t0 is placed at t=0 and can be derived from the velocity curve illustrated with a full line, at the time of the impact the operational sign of the velocity changes. The absolute value of the velocity decreases steadily on the forward path, namely left of the time of impact, the value of the velocity increases on the backward path, namely right of the time of impact. This is essentially allocated to the influence of the gravitation, the direction of the shot is from below to above in the illustration according to FIG. 1.

Figure 2:
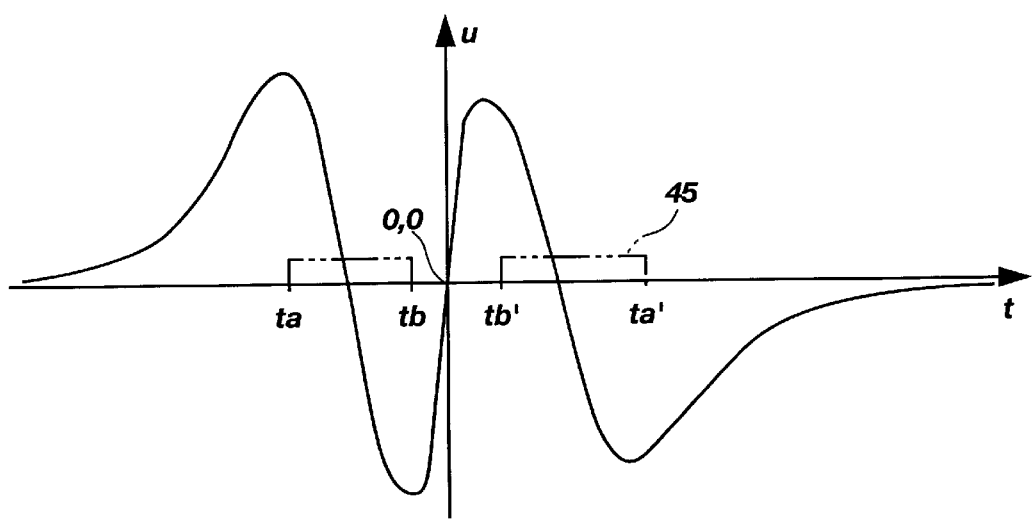

FIG. 2 illustrates a typical process of time of an induced tension. The conditions according to the device are such that the permanent magnet dips into the field of an induction coil and comes out of it, again. This leads to a zero crossing. A maximum is recorded at both ends of this zero crossing each. The forward- and backward path differ due to the altered direction of flying of the impact object in the operational sign. The values of the amplitudes on the backward path are smaller corresponding to the smaller velocities existing thereby. The maxima are not located necessarily at the same place as on the forward path.

Figure 3:
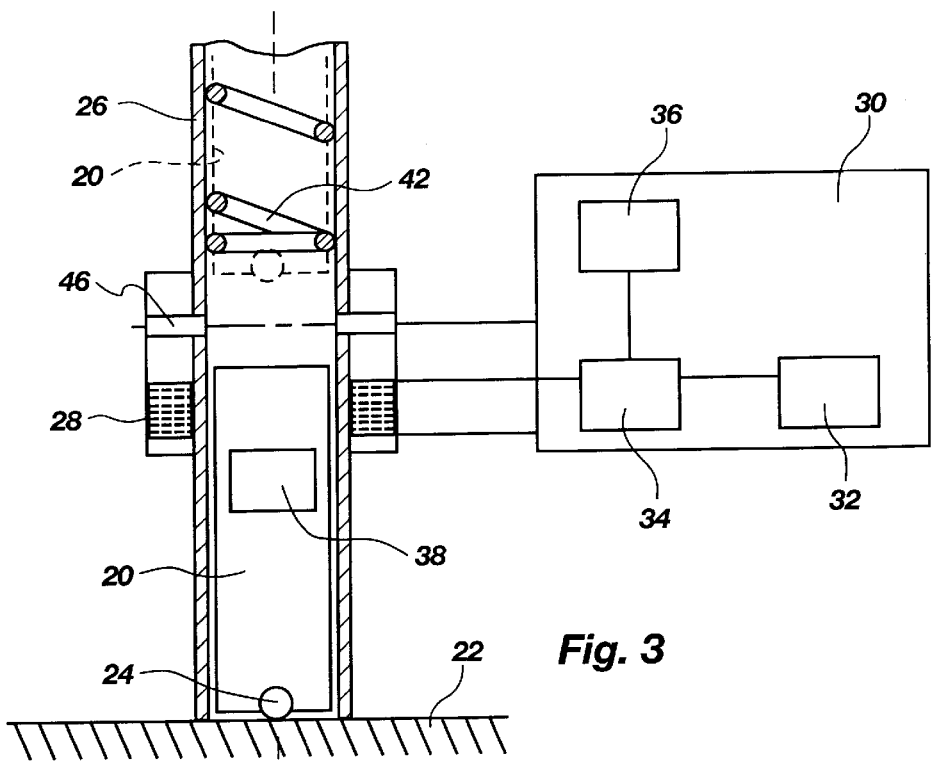

FIG. 3 principally illustrates the structure of a device for the operation of the procedure. An impact object 20 possesses a penetration object 24 at its final area, facing a workpiece 22 to be tested. In a practical embodiment it is formed as a hardened steel ball. The impact object 20 is lead freely movable, if possible, in a tubular case 26. This carries an induction coil 28, which is connected to an evaluation electronic 30, which has a memory 32, a micro processor 34 and a display 36.

A permanent magnet 38 is connected to the impact object 20. It is, just like the induction coil 28, centered around the axis 40 of the tubular case 26.

A light screw 46 is provided for a separate measurement of the location. There may also be two or more light screws provided.

As can be seen in FIG. 3, the light screw 46 consists of a transmitter, for example an IR-luminance diode and a receiver allocated to the same. In the locked state, the impact object 20 is located above the light screw, but as soon as it approaches the surface of the workpiece 22 sufficiently, it interrupts it and releases it in the further process, for example when it has a distance of 3 mm away from the workpiece 22 to it. On the backward path the same process occurs at the same locations but vice versa, the light screw is interrupted again, released respectively as soon as the impact object has traveled the corresponding distances of the backward path. The corresponding signal 45 of the light screw 46 can be superimposed in the process of the time of the induced tension, for example as a spike pulse or as additional superimposed information.

In the illustrated position the impact object 24 is positioned on top of the surface of the workpiece 22. This position illustrates an interstage during a measurement.

Before the measurement, the impact object 20 is at a distance to workpiece 22, this initial state is illustrated in FIG. 3 in a dotted line. In the initial state the back surface, opposite the workpiece 22, of the impact object 20 is stressed by a pressure spring 42, which is elastically prestressed. The impact object 20 is locked via a suitable, already known device. As soon as the locking device is released, the impact object 20 is accelerated in the direction of the workpiece 22, and caused by the force of the pressure spring 42 and in the embodiment shown additionally by the forces of gravity, based on the orientation illustrated in FIG. 3, meaning that the impact object 20 falls onto the workpiece 22 from above.

The pressure spring 42 does not accelerate the impact body 20 during the whole path, but only during a part of the path. This is a special characteristic of the invention. As can be seen from FIG. 3, the pressure spring 42 is only released up to a certain location, which is positioned 10 to 20 mm above the impact object 20 (in the position according to FIG. 3). On the part of the path of the impact object 20, on which the measurement, which is yet to be explained is located, the pressure spring 42 is not adjacent to the impact object 20.

A measurement is performed as follows: From the locked position of the impact object 20 already described, which is under the elastic pressure of the tensed pressure spring 42 and which is also in distance to the workpiece 22, the impact object 20 starts its forward path, when the locking is released. It is accelerated onto the workpiece 22 and strikes onto it with its penetration object 24. Thereby the forward path is completed. During the first part of the forward path the impact object 20 is accelerated by the pressure spring 42, but with a second part of the forward path no longer.

The impact object 20 rebounds off the workpiece 22 on a backward path, again, the backward path theoretically coincides with the forward path exactly, in the practical application minor derivations may occur. During the forward path and during the backward path, the permanent magnet 38 dips from the end of reel each time into the induction coil 38 and falls out of the same at the other end of the reel. Thereby the induced tension, as can be seen from FIG. 2, is received. To receive the distance- and time-dependency diagram according to FIG. 1 the direction of the shot needs to be turned around, therefore, the allocation according to FIG. 3 needs to be turned upside down.

As can be seen from FIG. 3, the length of the permanent magnet 38, measured in the direction of the axis 40, is about as big as the axial length of the induction coil 28, determined parallel to it. The actual distance of the two poles, positioned on the axis 40, of the permanent magnet 38 is slightly bigger than the geometrical length of the permanent magnet 38, the axial length of the induction coil 28 is therefore slightly bigger than the actual distance of the pole of the two poles of the permanent magnet 38.

The FIGS. 1 and 2 also have the drawn signal 45 of the light screw 46. By means of the figures the information about at least one definite point in time tL, to which the impact object is located at a certain location, is received in the time-dependency diagram of the FIGS. 1 and 2. A further determination of the location is received by the zero crossing of the induced tension. Thereby two points in time of the forward path and two points in time of the backward path are received, for which the corresponding location is known. For the location of the light screw, the corresponding value of the quantity of motion is given furthermore. There is no information for the location, where the zero crossing of the induction tension occurs, from the corresponding induction coil about the velocity at the location of the zero crossing, but it is possible to determine the velocity at the known location by means of additional mechanical means, for example a further induction coil, or by means of mathematical procedures. Thereby an extrapolation onto the quantity of motion at the time of impact is possible within the meaning of FIG. 1. This solution, just described, is based on the condition that, the process of time of the velocity v(t) in distance of the location of impact can be described by a straight line, as illustrated in FIG. 1.

If a higher accuracy is desired and/or one does not consider the already described approximation by means of a straight line as sufficient, measurements can be performed at three or more locations. It is advantageous, if a separate measurement of the location, for example via the described light screw, occurs at one location, where normally a maximum of the induced tension u(t) is to be expected.

Figure 4:
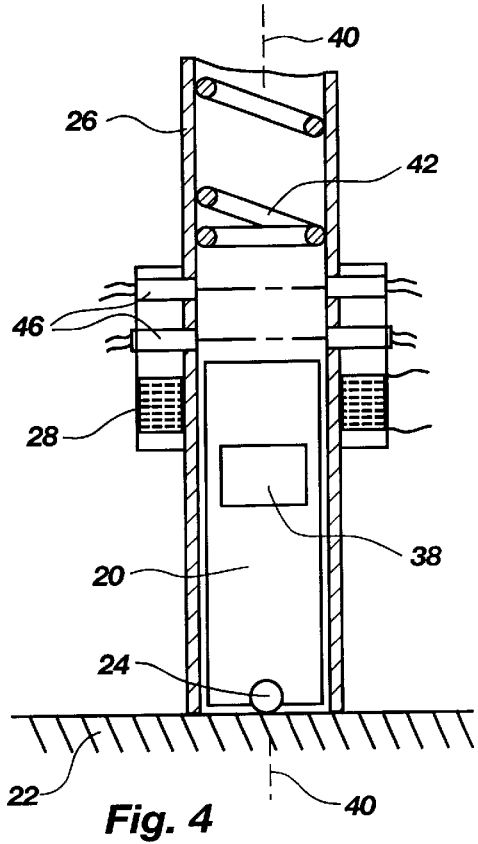

In the embodiment according to FIG. 4 two light screws are provided, both of the same kind as explained in FIG. 3. They are arranged geometrically at the tubular case 26 in such a way that on the forward path the maxima of the induced tension occur at their particular position. On the backward path the maxima, recorded in the time illustration, do not have to occur at the same locations as on the backward path. Exactly that kind of derivation is recorded via the concrete measurements of the location.

In the following, the evaluation of the results of the measurements are explained, as received with a device according to FIG. 4:

At the time of the impact t0=0 is valid, further the position to the time of impact is presumed as x0=0, the penetration is therefore neglected. Consequently negative time characteristics describe the forward path, positive ones the backward path, the same applies to the velocity, negative v-values describe the forward path, positive ones the backward path. The forward path is marked each time by the number 1 placed behind. Then x1(t) is the function of the location of the forward path, v1(t) the course of the velocity. The backward path is marked by the number 2, then v2(t) is the course of the velocity of the backward path. The position of the impact object can be recorded each time via the integration of the measured timely dependency of the velocity of the impact object v1(t) or v2(t) by means of the duration of time of the corresponding distance of the forward-, or the backward path.

The induction tension u(t) is measured. Its process of time is the following:

$$u(t)=c(x(t))\cdot v(t),$$

whereby c(x) represents a given function of the position of the impact object for the arrangement coil-impact object. c(x) corresponds to the course of the induction tension, when the impact object flies through the induction coil with a constant "unified velocity" c(t)=1, because then, there is a change of x(t)=t and therefore u(t)=c(x).

With the practical measurement of the hardness, u(t) is measured and one is inclined to derive v(t) therefrom. The value h=v2(0):v1(0) is of special interest, which is proportional to the hardness in Leeb.

Based on the measurements, at two locations a and b for the forward path and the backward path each time, a precise time arrangement of the time t to the location x is given each time, for both locations, for both locations each equals x1(ta)=x2(ta') and x1(tb)=x2(tb'). From the measured values for the induction tension u(t) for the two known locations of the forward path and the backward path, pairs of variates exist now each for the location and the corresponding value of the velocity. From that two values of the value h can be determined, as there are $$ha=v2(xa):v1(xa) \text{ and } hb=v2(xb):v1(xb).$$

From the two points ha and hb the value of h for the value x=0 can be calculated by linear extrapolation, the value represents the desired value of the hardness.

Figure 5:
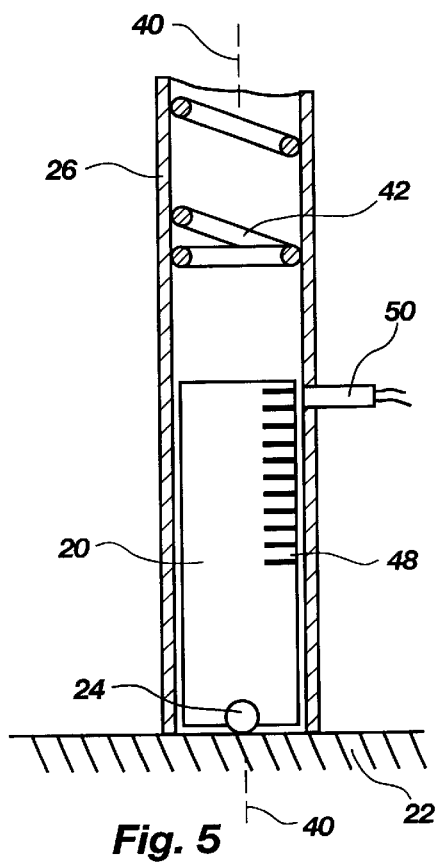

In the embodiment according to FIG. 5 the velocity is not recorded in an inductive way, but via a scale 48, which is arranged at the impact object 20. It is illuminated and scanned via a light receiver 50. The faster the impact object 20 runs along this arrangement, the more light/dark signals are received. Additionally the scale 48 is coded in such a way that at least two signals of location are received. In a simple embodiment the scale consists of equidistantly arranged black girders and white lines. At at least two locations additional marks are provided, there for example, the black girder is significantly smaller in the direction of the movement, an additional reflector is attached, the girder is longer or similar.

The value of the quantity of motion is either direct, or a proportional value to it, or it is in a solid functional dependency to it.

We claim:

1. A procedure for a hardness test of workpieces, in which an impact object is moved along a forward path into the workpiece to be tested in such a way, that the impact object strikes the workpiece, then rebounds off it and moves on a rearward path away from the workpiece; whereby the respective velocities of the forward path and the rearward path of the impact object are recorded by means of a nonintervening measuring device; whereby a measurement of the hardness of the workpiece is established by comparing the difference of the motion of the forward path and that of the rearward path; characterized by the fact that the velocities of motion are recorded on at least two locations of the forward path and on at least two locations of the rearward path, such that forces of gravity are taken into account at the time of measurement, and that each location of the forward path where the velocity of motion is recorded corresponds to a location of the rearward path.

2. The procedure according to claim 1, characterized in that the velocity of motion is recorded on at least three locations on the forward path and is correspondingly recorded in the same way on the rearward path.

3. The procedure according to claim 1, characterized in that the velocities of motion are each recorded electromagnetically, using a permanent magnet located in the impact object, and using a tubular case with an induction coil in which the impact object is movable.

4. The procedure according to claim 1, characterized in that the velocities of motion are recorded continually on the forward path and on the rearward path.

5. The procedure according to claim 1, characterized in that at least one signal locating device provides the determination of the location of the impact object, and provides the tension induced in a measurement process for a zero crossing.

6. A device for the operation of the procedure according to claim 1 with an impact object, which has a permanent magnet and a tubular case, which device encloses the impact object and in which the impact object is movable; characterized in that at least at two different locations in the tubular case, measuring devices are provided for the recording of a velocity of the impact object on the respective forward-and-rearward paths.

7. The device according to claim 6, characterized in that a pressure spring is disposed within the case, which has a distance of between 10 mm and 20 mm to the impact object located at the location of the impact of the direct device.

8. The device according to claim 6, characterized in that the devices for the recording of the velocities of motion have an electromagnetic capability.

9. The device according to claim 6, characterized in that the devices for the recording of the respective velocities of motion have means for the measurement of the location of the impact object.

* * * * *